United States Patent
Hovland et al.

(12) 
(10) Patent No.: US 6,251,076 B1
(45) Date of Patent: *Jun. 26, 2001

(54) MALE IMPOTENCE DIAGNOSTIC ULTRASOUND SYSTEM

(75) Inventors: Claire T. Hovland, Minnetonka; Jerome H. Abrams, St. Paul; Edward J. Wons, Minnetonka, all of MN (US)

(73) Assignee: UroMetrics Inc., St. Paul, MN (US)

( * ) Notice: This patent issued on a continued prosecution application filed under 37 CFR 1.53(d), and is subject to the twenty year patent term provisions of 35 U.S.C. 154(a)(2).

Subject to any disclaimer, the term of this patent is extended or adjusted under 35 U.S.C. 154(b) by 0 days.

(21) Appl. No.: 08/905,260

(22) Filed: Aug. 1, 1997

(51) Int. Cl.[7] .......................................... A61B 8/06

(52) U.S. Cl. .......................................... 600/454; 600/504

(58) Field of Search .................... 600/459–460, 600/453–456, 587, 504

(56) References Cited

U.S. PATENT DOCUMENTS

| | | |
|---|---|---|
| 3,661,146 | 5/1972 | Peronneau et al. . |
| 4,334,543 | 6/1982 | Fehr . |
| 4,428,385 | 1/1984 | Morales . |
| 4,469,108 | 9/1984 | Goldstein . |
| 4,474,187 | 10/1984 | Timm et al. . |
| 4,485,821 | 12/1984 | Iinuma . |
| 4,515,166 | 5/1985 | Timm . |
| 4,606,353 | 8/1986 | Timm . |
| 4,612,937 | 9/1986 | Miller . |
| 4,722,347 | 2/1988 | Abrams et al. . |
| 4,747,415 | 5/1988 | Laveisier . |
| 4,766,909 | 8/1988 | Timm et al. . |
| 4,848,361 | 7/1989 | Penney et al. . |
| 4,869,260 * | 9/1989 | Young et al. ...................... 600/453 |
| 4,911,176 | 3/1990 | Timm et al. . |
| 4,915,113 * | 4/1990 | Holman ............................... 600/460 |
| 4,928,706 | 5/1990 | Trick . |
| 5,205,292 | 4/1993 | Czar et al. . |
| 5,284,146 | 2/1994 | Czar et al. . |
| 5,398,216 | 3/1995 | Hall et al. . |
| 5,409,005 | 4/1995 | Bissonnette et al. . |
| 5,409,010 | 4/1995 | Beach et al. . |
| 5,437,187 | 8/1995 | Karbach et al. . |
| 5,443,069 | 8/1995 | Schaetzle . |
| 5,482,039 | 1/1996 | Place . |
| 5,562,097 * | 10/1996 | Yal ....................................... 600/457 |
| 5,565,466 | 10/1996 | Gioco et al. . |
| 5,931,783 | 8/1999 | Redano . |
| 5,947,901 | 9/1999 | Redano . |

FOREIGN PATENT DOCUMENTS

WO 92/09962 6/1992 (WO) .

OTHER PUBLICATIONS

Bassiouny, et al., "Penile Duplex Sonography in the Diagnosis of Venogenic Impotence," *Journal of Vascular Surgery*, vol. 13, No. 1, pp. 75–83, Jan., 1991.

(List continued on next page.)

*Primary Examiner*—Francis J. Jaworski
(74) *Attorney, Agent, or Firm*—Dicke, Billig & Czaja, P.A.

(57) ABSTRACT

An apparatus for diagnosing male impotence by measuring blood velocity in a cavernosal artery of a male penis includes at least one transducer for transmitting/receiving energy and reading corresponding Doppler effect to detect blood velocity in the cavernosal artery, a transducer housing for supporting the transducer in a substantially fixed orientation with respect to the penis as the transducer measures blood velocity in the cavernosal artery, and a fixing device, mechanically coupled to the transducer housing, to substantially mechanically fix the transducer housing in place with respect to the penis and hold the at least one transducer in a substantially constant angular orientation with respect to the cavernosal artery during an impotence diagnostic procedure. Corresponding methods are also disclosed.

37 Claims, 6 Drawing Sheets

OTHER PUBLICATIONS

Chen, M.D., Kuang–Kuo, Sonographic Measurement of Penile Erectile Volume, *Jounral of Clinic Ultrasound,* vol. 20, pp. 247–253, May 1992.

Cochlin, D.L., et al., *Urogenital Ultrasound, A Text Atlas,* pp. 257–258.

Gammelgaard, et al., "Transurethral and Transrectal Ultrasonic Scanning In Urology," *The Journal of Urology,* vol. 124, pp. 863–868, Dec., 1980.

Holm, et al., "Ultrasonically Guided Precise Needle Placement in the Prostate and the Seminal Vesicles," *The Journal of Urology,* vol. 125, pp. 386–388, Mar., 1981.

Kisslo, J., et al., ed., *Basic Doppler Echocardiography,* pp. 11–16 and 190.

Levine, et al., "Identification of a New Penile Duplex Ultrasound Vascular Flow Pattern," Proceedings of The American Urological Assocation, vol. 153, p. 330A, Apr., 1995 Supplement.

Levine, L.A., et al., "Measurement of Venogenic Impotence Penile Duplex Ultrasonography," *Journal of Urology,* 1990, 143: 211A.

Lue, T.F., et al., "Vasculogenic Impotence Evaluated by High–Resolution Ultrasonography and Pulsed Doppler Analysis," *Radiology,* 1985, 155: 777–81.

Lue, T.F., et al., "Functional Evaluation of Penile Arteries with Duplex Ultrasound in Vasodilator Induced Erection," *Urol Clin North Am* 1989, 16: 799–806.

Mueleman, et al., "Assessment of Penile Blood Flow by Duplex Ultrasonograph in 44 Men with Normal Erectile Potency in Different Phases of Erection," *Journal of Urology,* vol. 147, pp. 51–56, Jan., 1992.

Nelson Robert P., et al., "Determination of Erectile Penile Volume By Ultrasonography," *The Journal of Urology,* vol. 141, pp. 1123–1126, May, 1989.

Quam, J.P., et al., "Duplex and Color Doppler Sonographic Evaluation of Venogenic Impotence," *AJR,* 1989; 159: 1141–7.

Advanced Technology Laboratories Ultramark 9 Ultrasound System brochure, 1993.

Advanced Technology Laboratories C7–4 HDI Broadband Curved Array Scanhead brochure, 1993.

Advanced Technology Laboratories Ultramark 9 Digital Computed Sonography System brochure.

Medasonics Neuroguard Transcranial Doppler Noninvasive Blood Flow Monitoring System brochure.

Medasonic F3PA Doppler Fetal Pulse Detector Ultrasound Stethoscope brochure.

EPC–1 Bidirectional Vascular Doppler with Spectral Analysis Add–On Board Reference Manual, 1996.

\* cited by examiner

MALE IMPOTENCE DIAGNOSTIC ULTRASOUND SYSTEM

CROSS-REFERENCE TO RELATED APPLICATIONS

The subject matter of this application is related to the subject matter of U.S. Provisional Application No. 60/023,959, filed Aug. 9, 1996 and U.S. Provisional Application No. 60/041,361, filed Mar. 21, 1997, both of which are incorporated herein by reference and priority to both of which is claimed under 35 U.S.C. §119(e).

BACKGROUND OF THE INVENTION

1. Field of the Invention

The invention relates to an apparatus and method for diagnosing erectile disfunction, and more particularly, for diagnosing vasculogenic erectile disfunction by using Doppler frequency shift to measure penile blood velocity.

2. Description of Related Art

Male impotence is defined as the chronic inability to attain and/or maintain an erection of sufficient rigidity for sexual intercourse. This problem affects approximately 10 million American men, with increasing incidence in those of advanced age. Impotence is a source of great anxiety for many and is the subject of many thousands of visits to physicians and other medical professionals every year.

During a normal erection, neurochemical stimulation causes penile arterial inflow to increase in the paired cavernosal arteries. The result is increased blood flow into the corpora cavernosa. The subtunical venus plexus is compressed against the tunica albuginea, and venous outflow is reduced to trap blood in the corpora cavernosa. This combination of increased inflow and decreased outflow results in vascular congestion of the penis, tumescence, and rigidity sufficient for sexual intercourse. It is believed that abnormal reduction of blood flow to the cavernosal arteries and/or excess venal outflow, i.e. corporal venous leakage, are the primary physical causes of impotence. These abnormal blood flow characteristics to and from the cavernosal arteries can be caused by a number of factors, for example atherosclerotic vascular disease, traumatic arterial occlusive disease, or defective venoocclusive mechanisms.

By measuring blood velocity in the cavernosal arteries, duplex ultrasonography has been used successfully to diagnose inadequate arterial inflow and excessive outflow. Typically, a transducer emits ultrasound energy and a receiver receives ultrasound energy reflected from the blood. Electronic circuitry then measures frequency differences between the transmitted and received ultrasound energy, to calculate blood velocity. See, for example:

Bassiouny, et al., "Penile Duplex Sonography in the Diagnosis of Venogenic Impotence,"*Journal of Vascular Surgery* , Vol. 13, No. 1, pp. 75–83, Jan., 1991;

Cochlin, D.L., et al., *Urogenital Ultrasound, A Text Atlas*, pp. 257–258;

Kisslo, J., et al., ed., *Basic Doppler Echocardiography* , pp. 11–16 and 190;

Levine, L.A., et al., "Measurement of Venogenic Impotence Penile Duplex Ultrasonography," *Journal of Urology,* 1990, 143:211A;

Lue, T.F., et al., "Vasculogenic Impotence Evaluated by High-Resolution Ultrasonography and Pulsed Doppler Analysis," *Radiology,* 1985, 155:777–81;

Lue, T.F., et al., "Functional Evaluation of Penile Arteries with Duplex Ultrasound in Vasodilator Induced Erection," *Urol Clin North Am* 1989, 16: 799–806;

Meuleman, et al., "Assessment of Penile Blood Flow by Duplex Ultrasonography in 44 Men with Normal Erectile Potency in Different Phases of Erection,"*Journal of Urology*, Vol. 147, pp. 51–56, Jan., 1992; and Quam, J.P., et al., "Duplex and Color Doppler Sonographic Evaluation of Venogenic Impotence," AJR, 1989; 159:1141–7.

See also U.S. Pat. No. 5,482,039 to Place. All of the above-listed documents are incorporated herein by reference.

The general calculations involved in determining blood velocity using Doppler shift are well known in the art. See, for example, U.S. Pat. No. 4,722,347to Abrams and Hovland, which is incorporated herein by reference. See also U.S. Pat. Nos. 4,334,543, 4,485,821, 5,205,292, and 5,284, 146 , which are incorporated herein by reference. See also the following documents, which are attached to and form a part of the above-identified Provisional Application No. 60/023,959:

Advanced Technology Laboratories Ultramark 9 Ultrasound System brochure, 1993.

Advanced Technology Laboratories C7–4 HDI Broadband Curved Array Scanhead brochure, 1993.

Advanced Technology Laboratories Ultramark 9 Digital Computed Sonography System brochure.

Medasonics Neuroguard Transcranial Doppler Noninvasive Blood Flow Monitoring System brochure.

Medasonics F3PA Doppler Fetal Pulse Detector Ultrasound Stethoscope brochure.

One of the key variables necessary for proper velocity calculations is the angle between the direction of transmitted/received ultrasound waves and the blood flow path. To achieve accurate velocity determinations, this angle, hereinafter called the angle of incidence or Doppler angle, must be known accurately and/or maintained with some precision.

With conventional ultrasound devices, selection and precise maintenance of this angle of incidence are difficult. Many ultrasound devices suitable for measuring penile blood flow are handheld. An important limitation of handheld devices is that the angle of incidence varies unacceptably from reading to reading over time, or even during a single reading. This variability is a result of the instability and imprecision inherent with handheld devices. The urologist does not know what the angle of incidence is, and even if a desired angle is known, achieving that desired angle reproducibly on repeat measurements is very difficult during a diagnostic procedure requiring many separate measurements. Even if the relevant calculations eliminate the need to know the precise angle, e.g. by taking velocity ratios so as to effectively eliminate the angle variable, the angle must be held constant. This instability represents a significant disadvantage with previous ultrasonography devices, a disadvantage that is heightened when taking measurements with respect to a readily movable organ such as the penis.

A further disadvantage of prior art ultrasonography devices, and particularly ultrasonography devices used for penile blood flow measurement, lies in the current uncertainty in the medical community concerning the proper timing of blood velocity measurements during a diagnostic procedure. Typically, the urologist or other medical professional takes an initial cavernosal artery flow velocity measurement. Then, papaverine or another suitable vasodilating agent is injected or transurethrally administered to induce erectile response. Further ultrasonographic examination follows, with a series of velocity measurements being taken over time after the vasodilator is introduced and after subsequent self-stimulation by the patient. Some urologists believe that if blood velocity increase is less than 25%, the patient is probably impotent; if greater than 75%, the patient is probably healthy. For increases between 25% and 75%, the urologist likely will perform additional tests.

More specifically, the urologist measures peak systolic and end diastolic velocities before injection and at 5, 10, and 30 minutes after application of the vasodilating agent. Normal peak systolic velocity is considered by some medical professionals to be about 25 cm/sec. A resistance index is calculated as the difference between the peak systolic and end diastolic velocities divided by the peak systolic velocity, or R.I. =(Peak systolic velocity - End diastolic velocity) / Peak systolic velocity.

A resistance index approaching or equal to about 1 is considered to be indicative of a normal result.

Choosing the exact timing of the post-vasodilation measurements to achieve accurate diagnosis is the subject of the debate. For example, slower but otherwise normal erectile response often occurs in males of advanced age, so that premature ultrasonographic measurement might result in a false positive diagnosis. A need has arisen, therefore, to eliminate the uncertainties involved in examination timing.

SUMMARY OF THE INVENTION

To overcome the above and other disadvantages, an apparatus for diagnosing male impotence according to the invention includes at least one transducer for transmitting/receiving ultrasound or other suitable energy to detect Doppler shift, for calculation of penile blood velocity. A transducer housing supports the transducer in a substantially constant orientation with respect to the penis, substantially fixing the angle of incidence, that is, the angle between the transmitted/received ultrasound or other energy and the blood velocity vector. An acoustic coupling film can also be applied between the transducer and the penis, to enhance transmission of the ultrasound energy to/from the penis.

A fixing device is mechanically coupled to the transducer housing and at least partially surrounds the penis, to hold the transducer housing substantially steady and in place during an impotence diagnostic procedure. According to one embodiment, the fixing device includes a pressure balloon supported by a disposable housing, optimizing support of and frictional contact with the penis. According to another embodiment, an elastic strap is used to achieve this purpose. Alternatively, an adhesive tape mounts the transducer housing on the top surface of the penis. The fixing device according to the invention allows the apparatus to be secured to the penis for an extended period of time, allowing the angle of incidence to be substantially fixed and allowing continuous measurement and recording of data throughout an entire diagnostic procedure.

The transducer or transducers are movably mounted on the transducer housing, according to one embodiment, to allow lateral adjustment of the direction of ultrasound transmission. According to another embodiment the transducers are fixed within the housing. Using multiple transducers allows simultaneous measurement, or at least immediately sequential measurement, of penile blood flow in both cavernosal arteries.

The features of the invention summarized thus far can be used as part of a larger diagnostic system according to the invention, including, for example, monitors or other displays for continuously displaying velocity data or other related data. Additionally, the larger system can be designed to continuously record relevant data on a computer disk or a printer, for example, for later review and analysis; real-time imaging is not necessary. Both portable and desktop computer configurations are contemplated.

According to another aspect of the invention, a method of diagnosing male impotence includes positioning at least one transducer over the penis to transmit energy, such as ultrasound energy, into the cavernosal arteries. The transducer is preferably supported by a housing, either movable or fixed. The housing is secured to the penis with a fixing device, such as a pressure balloon, elastic strap, tape, or equivalent. Once the device is secured, blood velocity in the cavernosal arteries is measured continuously, preferably before, during and after administration of a vasodilating agent. According to one embodiment, the continuous measurement data is saved to disk and/or continuously displayed on e.g. a monitor screen.

To further aid diagnosis, the transducers can also be used to measure penis diameter during the diagnostic procedure, according to the invention. Graphical depictions of these penis diameter readings can then be correlated and displayed in relation to the blood flow velocity readings described earlier.

Embodiments of the invention provide significant advantages in that they are office-based, relatively inexpensive, easy to use, relatively independent of the operator, accurate over a wide range of velocities, and able to make reproducible measurements to evaluate the effectiveness of treatment over time.

BRIEF DESCRIPTION OF THE DRAWINGS

Embodiments of the invention will be described with reference to the figures, in which like reference numerals denote like elements, and in which.

DETAILED DESCRIPTION OF PREFERRED EMBODIMENTS

As described earlier, one of the principal advantages according to embodiments of the invention is that the elements used to transmit/receive energy to detect Doppler frequency shift, e.g. ultrasonic transducers according to one embodiment, are substantially fixed in position with respect to the penis and to the cavernosal arteries. This innovation in positioning defines and stabilizes the angle of incidence of the energy on the blood flow path in the cavernosal arteries, allows precise velocity measurements and, consequently, permits more accurate diagnosis by the urologist or other medical professional. Additionally, velocity measurements can be taken continuously, over an extended period of time, eliminating uncertainty regarding the timing of velocity measurements.

Embodiments according to the invention can be used to measure blood flow in a number of different areas and parts of the body. Flow can be measured in blood vessels of the arms, legs, fingers, neck, or other areas, for example. Thus, while preferred embodiments of the invention will be described with respect to the penis and to procedures for diagnosing impotence, the invention should not necessarily be construed as limited to those embodiments.

Figure 1:
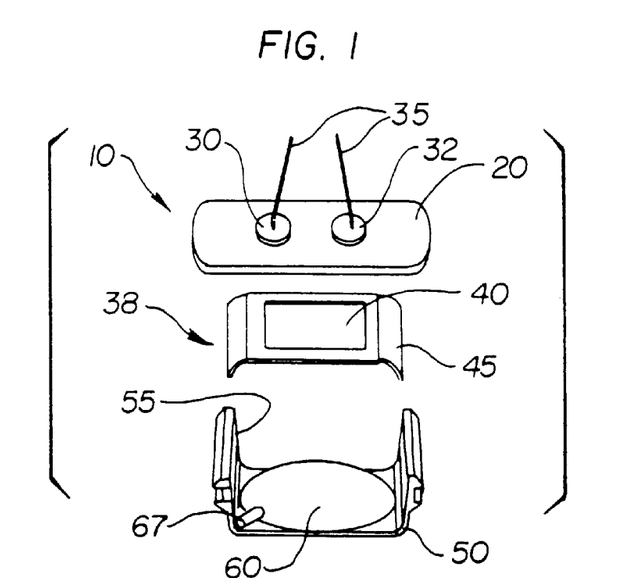
FIG. 1 is an exploded perspective view of an impotence diagnostic apparatus according to an embodiment of the invention.
Figure 2:
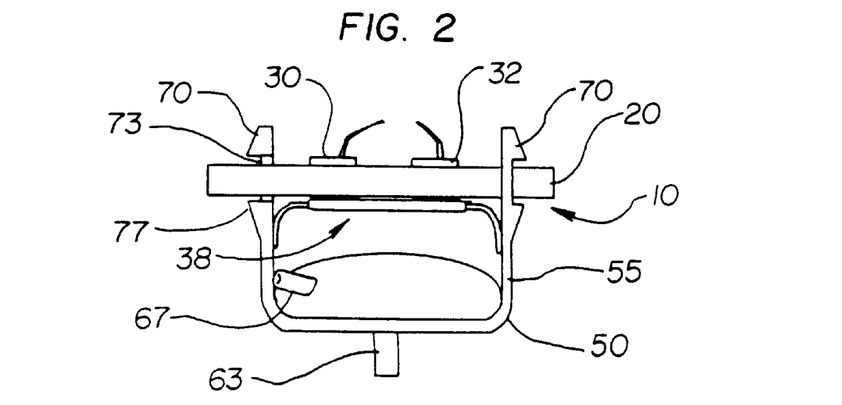
FIG. 2 is a side view of the FIG. 1 apparatus.

Turning to the figures, FIGS. 1–2 illustrate an impotence diagnostic probe apparatus 10 according to one embodiment of the invention. Probe 10 can be used as part of a larger impotence diagnostic system, as will be described.

Probe 10 includes transducer housing 20 for supporting at least one transducer, such as transducers 30, 32, at a substantially fixed angle of incidence. According to one embodiment, transducers 30, 32 transmit ultrasound energy, but any other transmit/receive scheme known to be functional in a Doppler-shift detection environment can be used, for example, other sonar-type or radar schemes.

Transducers 30, 32 (or their equivalents in non-ultrasound systems) are set at respective angles with respect to the penis, to create a known angular orientation with respect to the blood flowing in the cavernosal arteries, that is, a known angle of incidence. Coaxial cables 35 or other devices/systems connect transducers 30, 32 to electronics (not shown) that direct the transmission and reception of the ultrasound signals, and calculate and display Doppler frequency shift, blood velocity measurements, and/or other data.

According to a preferred embodiment, each transducer 30, 32 is a continuous wave, split-D transmitter/receiver. Each transducer is effectively split into two separated sides, with one side continuously transmitting and the other side continuously receiving. The split-D configuration is particularly advantageous, because it eliminates many of the transmitter-receiver angular alignments and other adjustments necessary with otherwise separated transmitter/receiver pairs.

Transducers 30, 32 can also be used in what is known as an A mode, using ultrasound or other energy to take various relevant distance measurements. Thus, the changing diameter of the cavernosal arteries can be measured and displayed, as can the diameter of the penis itself to reflect changing penile tumescence. Visual confirmation of vessel location is also provided. Measuring and displaying these values in conjunction with blood velocity values over time provides the urologist with an additional diagnostic tool. The A-mode measurement can also be used for accurate alignment of the ultrasound (or other) beam with respect to the cavernosal artery.

Of course, other transducer types and configurations are possible. Single-transducer embodiments are contemplated, for example pulse-wave piezoelectric devices in which a transmit mode is followed by a rest mode, and then a reception mode for receiving the reflected energy. The resulting combination of pulses requires the urologist to precisely set the focus depth, a requirement that is somewhat disadvantageous for the reasons described earlier. Whatever transducer arrangement is used, the angle of incidence is mechanically defined and substantially fixed with respect to the blood flow direction in the cavernosal arteries.

Figures 10, 11, 12, 13:
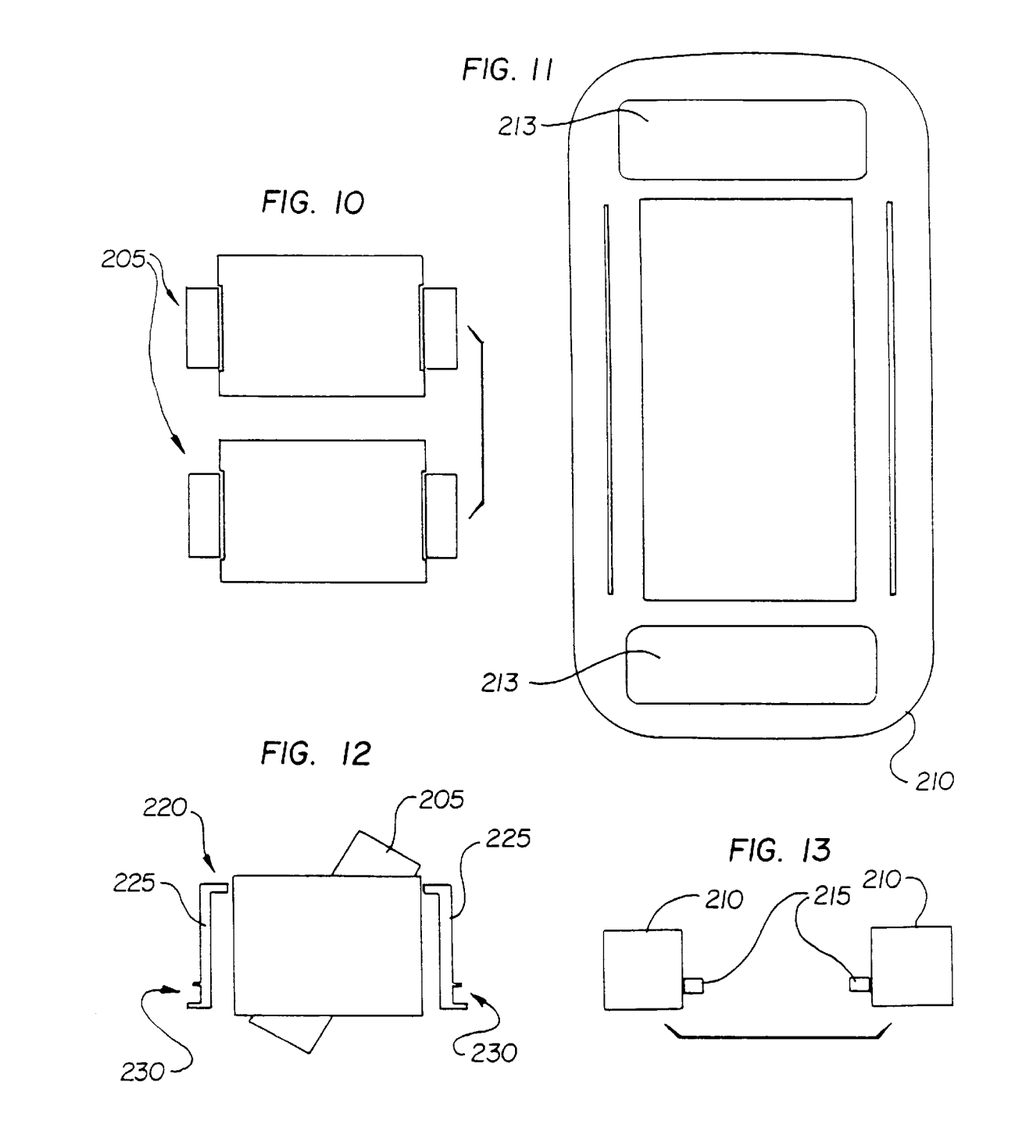
FIG. 10 is a top view of a transducer pair according to an embodiment of the invention.
FIG. 11 is a top view of a transducer housing according to an embodiment of the invention.
FIG. 12 is a side view of the FIG. 10 transducer pair.
FIG. 13 is a side view of the FIG. 11 transducer housing.

A continuous-wave ultrasound or other-type system with separate transmit and receive transducers, one on top of the penis and one on the bottom, is also contemplated. One particular example according to this embodiment will be described below with respect to FIG. 10.

Two transducers 30, 32 are illustrated in FIG. 1, one for each cavernosal artery. Using two transducers allows measurement, display and comparison of blood flow velocity in both arteries, either sequentially or simultaneously, both before and after vasodilation. Continuous peak systolic and end diastolic velocities, as well as accelerations, can be measured/calculated and displayed with respect to both arteries. Alternatively, of course, a single transducer or more than two transducers also can be used, to measure flow in various vessels at various locations. For example, an apparatus according to the invention also can be used to take measurements with respect to the urinary tract.

Transducers 30, 32 preferably are off-the-shelf components available on the open market from companies such as Blatek, Inc., of State College, Pennsylvania. Such ultrasound transducers typically have concave lenses in front, which focus the sound waves at the desired depth, here, in this case, the depth of the cavernosal artery.

Supplemental lens(es) may also be used to bend the ultrasound beam to the desired angle of incidence. According to one embodiment, the supplemental lens(es) are disposed in the air gap that otherwise would be created between the transducer and the patient's body, reducing the amount of gel or other acoustic filler material needed there. In accordance with Snell's law, the difference in the speed of sound between the lens(es) and the patient's tissues affects the amount of bend in the ultrasound beam as it passes into the tissues. Thus, the supplemental lens(es) allow the angle between the housing of the transducer and the tissues to be shallower than e.g. 60 degrees, providing a more compact overall mechanism.

As mentioned above, an acoustic filler material is desirable for use with embodiments of the invention. Because air is a relatively poor conductor of ultrasonic energy, a filler material is generally needed to direct the ultrasound into the patient's tissues with minimal attenuation.

One such material suitable for use according to the invention is a noninvasive hydrogel skin pad from LecTec Corporation, Minnetonka, Minnesota. As shown in FIGS. 1–2, skin pad 38 includes film material 40 surrounded by border 45. According to a preferred embodiment, both the top and bottom sides of film 40 and border 45 are sticky, to securely adhere to the surface of the penis. Pad 38 preferably is a disposable, single-use component, to promote cleanliness and reassure the patient that parts of probe 10 in direct contact with the penis are sanitary/sterile.

Instead of or in addition to pad 38, it is also possible to use a medium- or high-viscosity ultrasound transmission gel such as OMNIGEL® from Echo Ultrasound, Reedsville, Pa.

Once the urologist or other medical professional places pad 38 (or other filler) directly on the top of the penis, transducer housing 20 is placed on top, with transducers 30, 32 directly contacting film 40 for optimal acoustic coupling. The medical professional then places a fixing device around the lower surface of the penis to secure the transducer housing in place over the penis. According to the embodiment of FIGS. 1–2, the fixing device comprises disposable lower housing 50, which is secured to transducer housing 20 in a manner to be described.

Disposable lower housing 50 includes two upstanding sidewalls 55, between which is supported disposable pressure balloon 60. Pressure balloon 60 receives the patient's penis and conforms to its shape, expanding along the base of housing 50 and even up sidewalls 55 as needed. As the penis increases in size during periods of erectile response, pressure balloon 60 maintains the penis in substantially constant pressure contact with transducers 30, 32, via film 40. Balloon 60 holds the penis in position as it grows, such that side-to-side shifting is substantially prevented. A substantially fixed relationship between the penis and transducers 30, 32 thus is maintained.

According to one embodiment, balloon 60 has slots on opposite ends thereof, to receive and accommodate sidewalls 55 of housing 50. During assembly of the apparatus, balloon 60 is merely slipped into position over sidewalls 55 for a secure and steady fit on lower housing 50. Balloon 60 preferably forms a substantial U-shape against the base of housing 50, riding up sidewalls 55, to center and comfortably hold the penis within housing 50. Balloon 60 maintains substantially constant pressure between the transducers and the penis, without occluding blood flood.

According to one embodiment, balloon 60 includes balloon fill valve 63 and constant pressure relief valve 67, to maintain a constant, desired pressure in balloon 60. Alternatively, valves 63, 67 need not be used, to eliminate the number of parts associated with balloon 60 and the associated increased complexity and cost.

As shown in FIG. 2, lower housing 50, pad 38 and transducer housing 20 are connected together by linking portions 70 of sidewalls 55. Linking portions 70 include central recesses 73 and opposite tapered portions 77, permitting easy insertion into and retainment within corresponding slots (93, shown in FIG. 3) through transducer housing 20. Linking portions 70 preferably are one piece with sidewalls 55. Alternatively, transducer housing 20 and/or sidewalls 55 of lower housing 50 can include structure providing vertical adjustability with respect to each other, to adjust the size of the space between lower housing 50 and transducer housing 20. This structure can take the form of a toothed section extending toward housing 20 on or near sidewalls 55, for example. A corresponding section, in the form of a gear, ratchet wheel, and/or pawl, for example, is supported by transducer housing 20 and matingly engages the toothed section associated with sidewalls 55. This structure locks lower housing 50 in a desired position with respect to transducer housing 20, yet allows easy adjustability.

Housings 20, 50 and link members 70 preferably are formed of injection-molded plastic, but of course other suitable materials, such as nylon or various polymers or metals, for example, also can be used.

Figure 3:
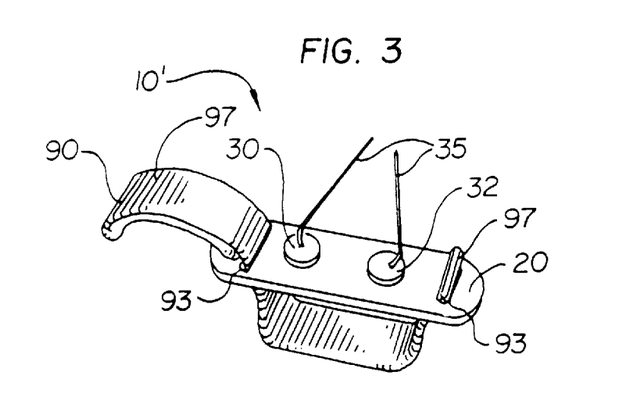
FIG. 3 is an upper perspective view of an impotence diagnostic apparatus according to an alternative embodiment of the invention.
Figure 4:
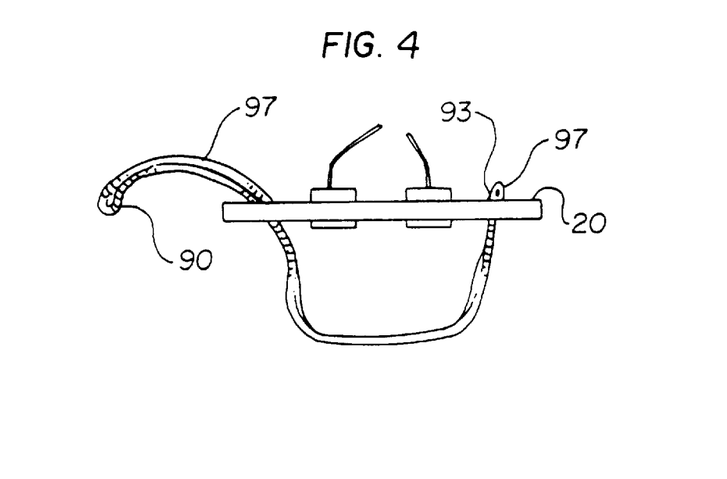
FIG. 4 is a side view of the FIG. 3 apparatus.
Figure 5:
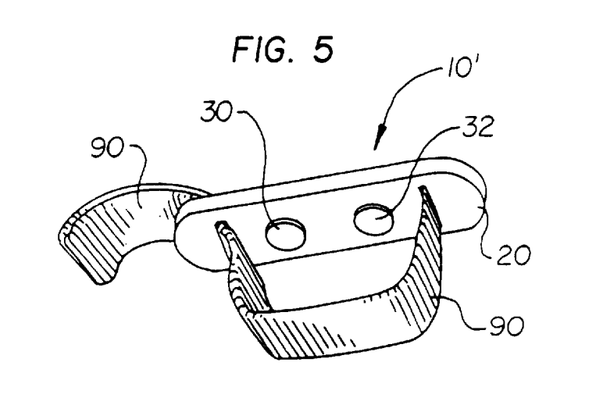
FIG. 5 is a lower perspective view of the FIG. 3 apparatus.

FIGS. 3–5 show an alternative probe embodiment 10', in which the fixing device for securing transducer housing 20 in place comprises strap 90, such as an elastic, paper, and/or cloth type strap, optionally with e.g. Velcro, tape or other type fastening devices for achieving a snug fit around the penis. Ends 97 of strap 90 pass through slots 93 in transducer housing 20, allowing easy adjustment into frictional engagement with the penis. Although strap 90 according to this embodiment is potentially constrictive and may not be as comfortable for the patient as the previously described embodiment, it has the advantage of being simple to adjust and simple to manufacture. It also is disposable, like housing 50 of the previous embodiment. Pad 38 is also useable in connection with this embodiment, but is not illustrated to simplify the drawings.

Other devices for securing transducer housing 20, or a similar transducer support, are contemplated. For example, a double-sided adhesive tape can be applied to the top side of the penis, without necessarily extending to the underside of the penis, to hold the transducers in place.

Whatever fixing device is used, it is desirable to position transducer(s) 30, 32 to straddle the dorsal blood vessels extending along the top of the penis, providing a relatively unobstructed ultrasound path to the cavernosal arteries. To this end, transducer housing 20 can include a central hinge. The two pivoting legs of housing 20 thus created permit the transducers to be positioned as desired, for example at 10o'clock and 2 o'clock positions, around the upper circumference of the penis. The angle of incidence, however, remains fixed at e.g. 60°.

Figure 6:
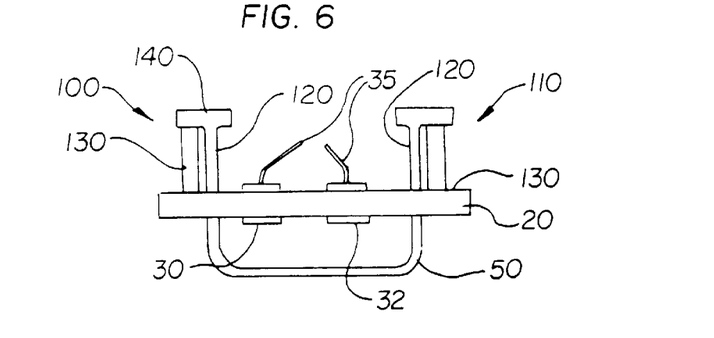
FIG. 6 is a side view of an impotence diagnostic device according to an alternative embodiment of the invention.
Figure 7:
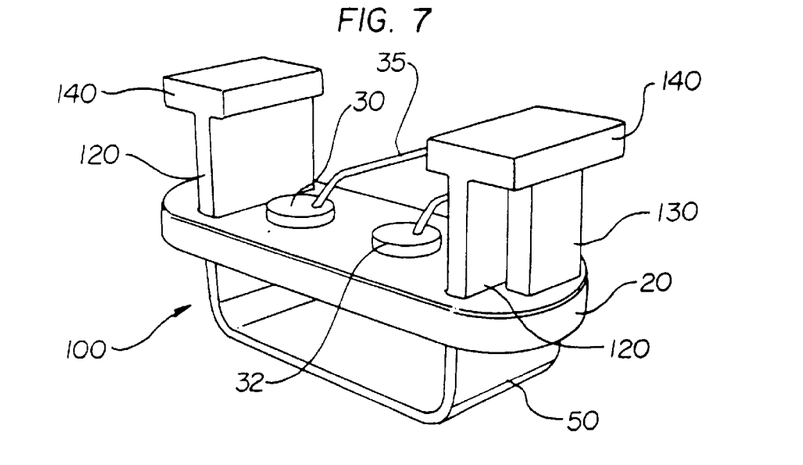
FIG. 7 is a perspective view of the FIG. 6 apparatus.
Figure 8:
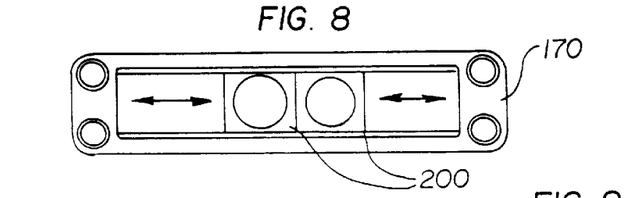
FIG. 8 is a top view of a transducer housing of an impotence diagnostic apparatus according to an alternative embodiment of the invention.
Figure 9:
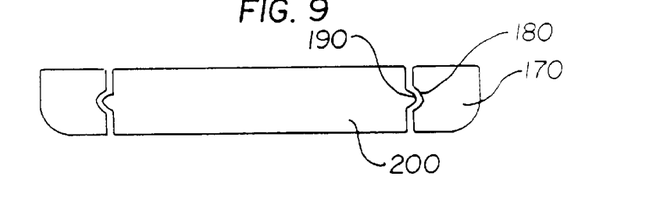
FIG. 9 is an end view of the FIG. 8 apparatus.

FIGS. 6–7 show an alternative diagnostic probe 100, which includes a transducer housing 20 that is similar or identical to the previous embodiments. Probe 100, however, additionally includes spring mechanism 110 to urge lower housing 50 into engagement with the penis, as will now be described. Spring mechanism 110 includes compression springs 130, connected to upstanding ends 120 of lower housing 50 via connecting pieces 140. Springs 130 bias connecting piece 140 and upstanding ends 120 vertically upward, urging lower housing 50 towards transducer housing 20 to compress the penis therebetween. Springs 130 (as well as strap 90 of the previous illustrated embodiment) are of course governed by Hooke's law; thus the pressure between the transducer and the penis changes depending on the size of the penis and consequent displacement of springs 130. FIGS. 8–9 show an alternative transducer housing embodiment. Transducer housing 170 defines an open frame and includes longitudinally extending grooves 180, into which fit corresponding tongue members 190 of individual transducers 200. Transducers 200 thus are slidable within transducer housing 170 into a desired position with respect to each cavernosal artery as needed, e.g. to adjust to a particular patient's anatomy. Thus, the individual transducers are laterally adjustable, while the housing maintains the angle of incidence substantially constant at about 60°, or another desired angle.

FIGS. 10–13 show a more detailed example of this type of structure. Transducers 205 are supported by transducer housing 210, which includes longitudinally extending rails 215. Transducers 205 include respective subhousings 220 with substantially rigid but bendable fingers 225, which carry riders 230 for slidably engaging rails 215. Fingers 225 can be squeezed together, substantially disengaging riders 230 from rails 215. Upon release, fingers 225 snap back to their original positions, creating a friction fit between riders 230 and rails 215. According to one embodiment (not shown), rails 215 and riders 230 are formed with a series of mating ridges or teeth extending along their lengths, to secure the transducers in a substantially fixed lateral position in housing 210 yet readily permit disengagement of riders 230 and rails 215 for lateral adjustment. Transducer housing 210 also includes slots 213 for receiving upstanding sidewalls 55 as shown in previous figures, for example. Housing 210 and subhousing 220 can be made of a plastic-type material or the like.

Figure 14:
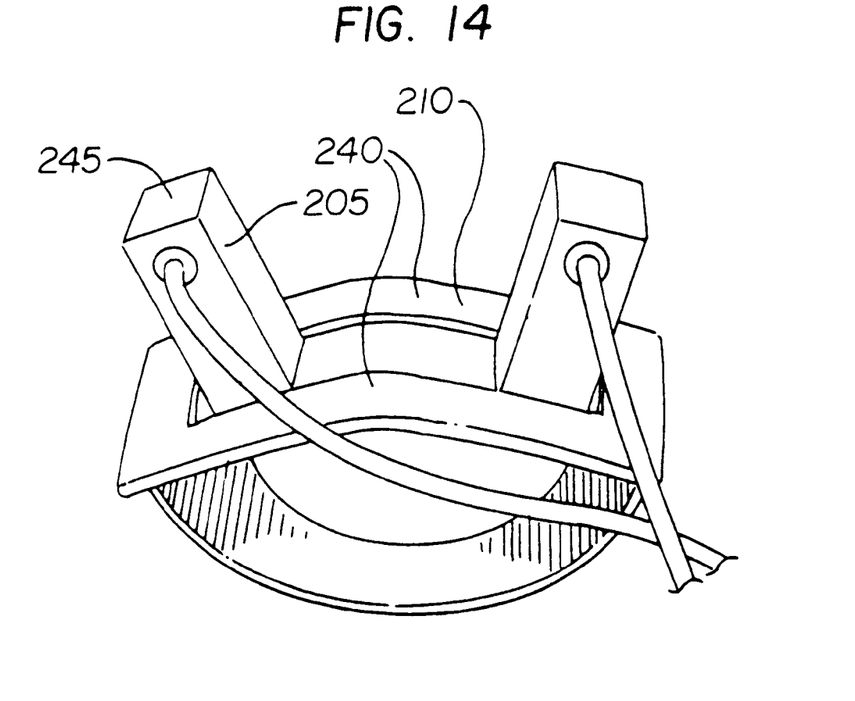
FIG. 14 is a perspective view of an alternative transducer housing embodiment of the invention.

FIG. 14 shows an alternative embodiment of transducer housing 210. Transducer housing 210 includes a central bend 240 that is substantially fixed to form a desired angle, e.g. 150°. Each "leg" of transducer housing 210 thus drops about 15° below the horizontal or other reference plane. Central bend 240 positions transducers 205 at about 10 o'clock and 2 o'clock on the penis, avoiding interference with the dorsal blood vessels and also reducing the potential "teeter-totter" effect present with a straight transducer housing 210. The angle of incidence remains fixed at e.g. 60°. Transducers 205 also preferably include arrows or similar markings 245 to indicate proper orientation of transducer housing 210 with respect to the patient. Transducer housing 210 can be positioned, for example, such that arrows 245 point away from the patient.

Figure 15:
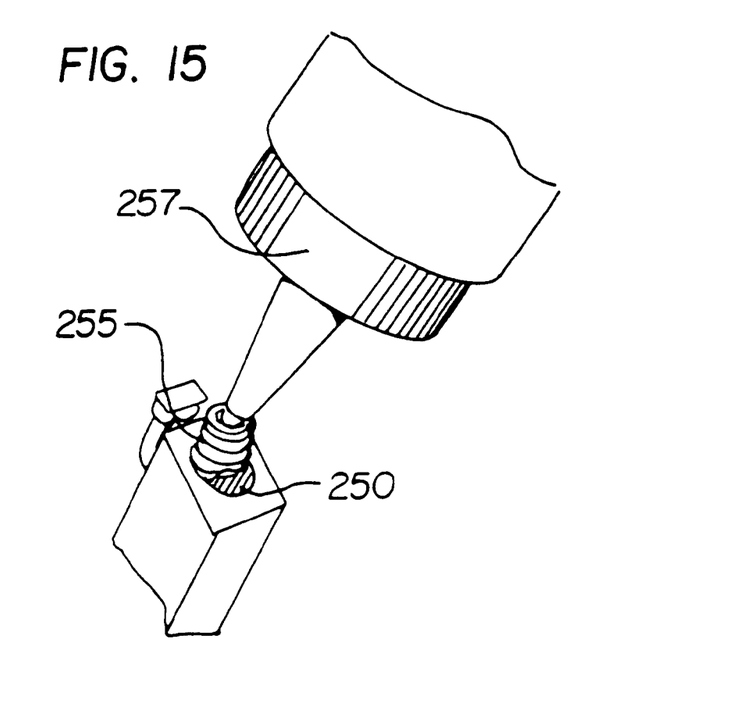
FIG. 15 is a perspective view of a transducer embodiment of the invention.

As shown in FIG. 15, according to one embodiment, transducers 205 include gap 250 for accommodating gel 255 or similar acoustically conductive material, dispensed by a suitable dispenser 257. Gap 250 should be completely filled with gel 255, to prevent air bubbles which block transmission of ultrasound signals. Gel 255 can be applied before transducer 205 is inserted into transducer housing 210, or afterwards.

Other aspects of the FIGS. 10–15 embodiments are as shown and discussed with respect to previously described embodiments.

Figure 16:
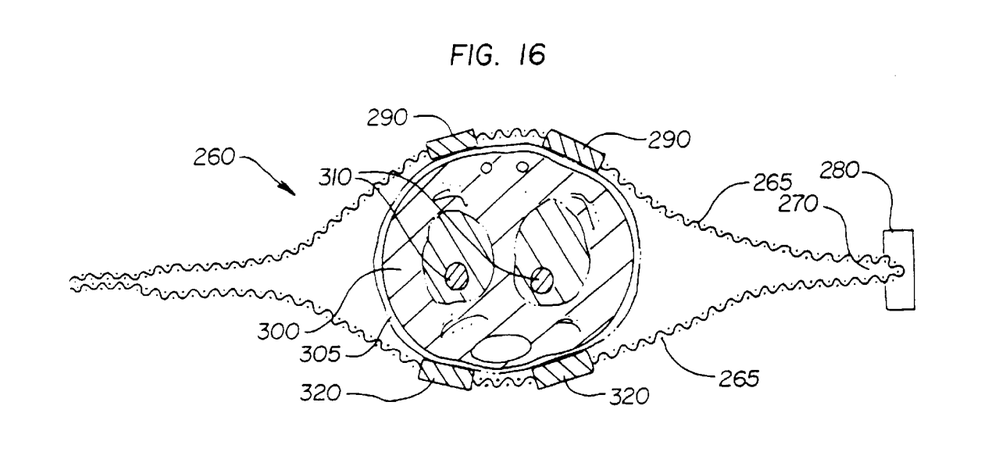
FIG. 16 is a cross-sectional view of an impotence diagnostic apparatus in a use position, according to an embodiment of the invention.

FIG. 16 shows an alternative diagnostic probe embodiment 260, which has separated transmit and receive transducers, as discussed earlier. Probe 260 is of relatively simple construction, with one or two elastic straps 265 secured together at ends 270 by a tightening and securement device 280. Straps 265 hold transducers 290, which according to one embodiment are transmit transducers, in a desired, substantially fixed position on the top surface of penis 300 relative to cavernosal arteries 310. Elastic straps 265 also hold transducers 320, e.g. receive transducers, in a substantially fixed position on the lower surface of penis 300. According to one embodiment, penis 300 is wrapped with a somewhat sticky cloth or cloth-like material 305 before bands 265 are tightened, to improve patient comfort and better hold the bands and transducers in place. Elastic bands 265 provide compression and expansion as needed to accommodate the changing size of the penis.

Alternatively, of course, straps 265 can be used to hold just two transducers, or even a single transducer, instead of the four separate transducers illustrated in FIG. 16. Although significant mechanical angular adjustment is necessary with this embodiment to achieve the desired angle of incidence and optimal beam positioning, this embodiment is of simple and low-cost construction.

Figure 17:
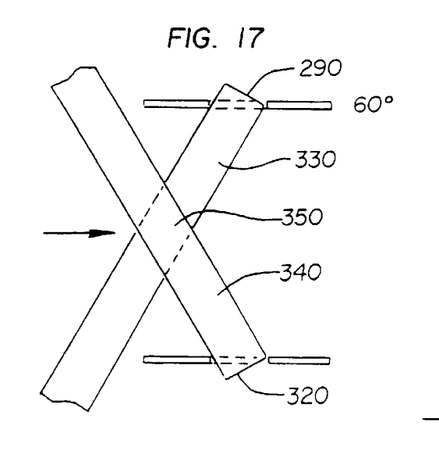
FIGS. 17–18 are views showing areas of ultrasonographic beam intersection, according to an embodiment of the invention.
Figure 18:
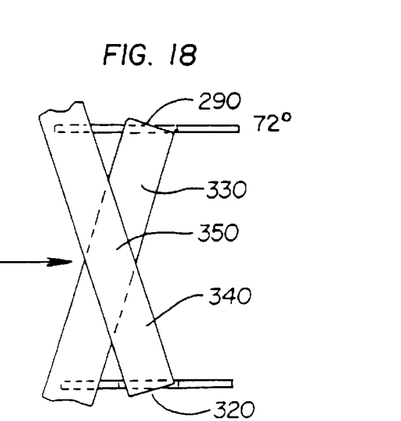

FIGS. 17–18 show transmit and receive transducer paths 330, 340, associated with transmit and receive transducers 290, 320 of FIG. 16, for two angles of incidence: 60 degrees and 72 degrees, respectively. Paths 330, 340 define intersection regions 350, which vary in size and positioning depending upon the angle of incidence, and which are positioned to intersect the cavernosal artery in which blood flow velocity is being measured.

The angle of incidence depicted in FIG. 17, 60 degrees, is preferred. As angle of incidence increases, Doppler shifting effect diminishes, to the point where at 90 degrees, there is zero Doppler shift. As the angle of incidence decreases, on the other hand, the sonographic or other energy must travel through tissue for a greater distance before hitting the intended target area. That travel is highly attenuative, and signal loss ultimately occurs. 60 degrees has been found to be a preferable angle of incidence to minimize these disadvantages.

As indicated above, the electronics associated with the chosen probe embodiment perform a wide variety of desired calculations and display graphical representations of a wide variety of variables, as chosen by the urologist or other medical professional. Control electronics components useable according to the invention can be purchased from a variety of companies. A graph of velocity versus time for both cavernosal arteries can be displayed, either simultaneously or sequentially at the direction of the medical professional, during the course of the procedure or afterwards. Additionally, the velocity displays can be correlated with electrocardiogram and/or pulse oximetry readings to depict variations in blood velocity with respect to heartbeat. Penile diameter readings can also be displayed and correlated.

The displayed graphical information can be in a number of different formats on the display screen. For example, a spectral distribution graphical mode displays a gray scale that represents all of the Doppler frequencies. The greater the shift in frequency, the greater the distance from the baseline on the display screen. In a mean frequency mode, the statistical mean of the Doppler frequencies is displayed, for example as a colored line. In the show index mode, pulsatility, resistance, spectral broadening and heart rate values are displayed. The maximum frequency mode displays maximum frequency shift, for example as a colored line. Finally, the mode frequency graphical mode displays the single frequency that occurs most often during a sample, again as a colored line, for example.

The spectral distribution, maximum frequency and mean frequency displays can be used simultaneously to determine signal quality. When adjusting the transducer(s) to measure velocity in the cavernosal arteries, a maximum gray-scale (spectral distribution) signal should be displayed. If the signal is of a good quality, the maximum frequency display and the mean frequency display should follow the wave form displayed by the spectral distribution. The mean frequency should be lower than the maximum frequency, and the distance between the two should be relatively constant.

Although the probe according to the invention can be placed at any location on the shaft of the penis, it is preferably placed as close as possible to the base of the penis during the diagnostic procedure, allowing full accessibility for vasodilator introduction or self-stimulation. This placement also allows for duplex scanning to be conducted in the remainder of the penis, to look for damage within the penis as needed. Embodiments of the invention, therefore, provide optimum penile accessibility. Placement at the base also provides greater stability. Proper initial placement can also be verified by using headphones or external speakers to broadcast the "whooshing" sound detected as the ultrasound intersects the cavernosal arteries.

For the typical patient, it is fair to assume that the cavernosal arteries run parallel to the surface of the penis and actual blood flow velocities can be determined. Even in the irregular case, where the cavernosal arteries deviate from true parallel with the surface, the medical professional can make an accurate diagnosis, according to embodiments of the invention. Because the angle of incidence is held substantially constant during the time of the diagnostic procedure, impotence or health can be diagnosed with reference to velocity ratios, i.e. the percentage increase in blood velocity over time, eliminating the need to know the angle of incidence ultra-precisely. Relative velocity calculations are independent of the angle of incidence, but only when the angle is kept constant by mechanical fixturing during the diagnostic procedure as with embodiments of the invention. Acoustic Output Levels According to one continuous-wave model, the following holds true:

|  | Max. Value | $W_O$ | $f_c$ | $Z_{sp}$ | $X_{-6}, Y_{-6}$ | EPD |
|---|---|---|---|---|---|---|
| $I_{SPTA3}$ | 78 (+22.6/−14.0) mW/cm$^2$ | 1.6 (+0.72/−0.29) mW | 7.85 MHz | 11 mm | 1.0 (=0.12/−0), 0.8 (+0.10/0) mm | .76 × .38 cm |

The values in parenthesis are measurement errors calculated by adding worst case error values for hydrophone, measurement, calculation and position uncertainties, using the "sum of squares" method. Velocity Ranges Maximum range of velocities detectable at maximum Doppler frequency display range:

±32kHz Doppler shift at 0°:±3meters/second(±7cm/s)

±32kHz Doppler shift at 30°:±3.5meters/second(±40cm/s)

Explanation of Terms

Max. Value The maximum values given above were derated from intensities measured in water. For the derated intensities, tissue attenuation is taken into account. Tissue attenuation is estimated at 0.3 dB / cm x MHz. Attenuation is calculated for the focal depth, i.e. the point of highest ultrasound intensity ($Z_{sp}$). The spatial peak temporal average intensity ($I_{SPTA}$) measured in water is decreased by the loss due to attenuation which leads to the derated value ($I_{SPTA3}$)

$W_O$ This value represents the overall acoustic power delivered by a transducer and is calculated by integrating the output intensity over the complete ultrasound beam.

$f_c$ The center frequency of the transducer. This value is calculated from a Fourier analysis of the spectrum produced by a transducer and can differ slightly from the actual working frequency.

$Z_{SP}$ This is the axial distance that is used to calculate the aerated intensity. It is the distance from the transducer surface at which the peak value for the derated intensity occurred.

$X_{-6}$, The dimensions of the ultrasound beam measured at the distance of $Z_{SP}$. The values indicate the width of the beam with boundaries defined by the acoustic intensity being 6 dB less than the maximum intensity.

EBD Entrance beam dimensions. The dimensions of the ultrasound beam at the surface of the transducer. Transducers have a "split-D" configuration; transmitting and receiving elements each have the form of a half-circle. Numbers represent diameter and radius of the half-circle.

While the invention has been described with respect to preferred embodiments, the invention is not intended to be limited to those embodiments. Various modifications and changes will be readily apparent to those of ordinary skill upon reading the application. Many elements of the various embodiments described above can be mixed and matched. For example, pad 38 can be used with the embodiment of FIGS. 8–9, even though such use is not specifically described in the text. Film 40 and border 45 can also be applied separately instead of in a onepiece pad. Further, as referenced earlier, embodiments of the invention have application to other areas of the body and other diagnostic procedures. Various other modifications and changes may occur to those skilled in the art without departing from the spirit and scope of the invention as defined in the following claims.

What is claimed is:

1. An apparatus for measuring blood velocity in a cavernosal artery of a male penis, the apparatus comprising:

at least one transducer for transmitting/receiving energy and reading corresponding Doppler effect to detect blood velocity in the cavernosal artery both when the penis is in an erect state and when the penis is in a flaccid state;

a substantially rigid transducer support housing for supporting the at least one transducer in a substantially fixed orientation with respect to the penis as the at least one transducer measures blood velocity in the cavernosal artery, the at least one transducer being adjustable with respect to the transducer support housing; and a fixing device, mechanically coupled to the transducer support housing, to substantially mechanically fix the transducer support housing in place with respect to the penis and hold the at least one transducer in a substantially constant angular orientation with respect to the cavernosal artery during a measurement procedure, the fixing device being constructed to accommodate the changing size of the penis between the erect and flaccid states such that the at least one transducer remains aligned with the cavernosal artery as the diameter of the penis changes.

2. The apparatus of claim 1, wherein the fixing device comprises a pressure balloon supported by a disposable housing, to maintain substantially constant pressure between the penis and the at least one transducer.

3. The apparatus of claim 1, wherein the fixing device comprises a strap for wrapping around the penis.

4. The apparatus of claim 3, wherein the strap is an elastic strap constructed to expand to accommodate the changing diameter of the penis from the flaccid state to the erect state.

5. The apparatus of claim 1, wherein the at least one transducer comprises at least two transducers, further wherein the at least two transducers are shiftable relative to each other to aim the transmitted/received energy to a desired location.

6. The apparatus of claim 5, wherein each transducer is supported by a subhousing, each subhousing being slideably supported by the transducer support housing, each transducer and respective transducer subhousing being shiftable relative to the transducer housing to aim the transmitted/received energy to a desired location.

7. The apparatus of claim 6, wherein each transducer subhousing comprises at least one rider and the transducer support housing includes at least one corresponding rail, the rider of each transducer subhousing sliding along the rail of the transducer housing for laterally adjusting the respective transducer position.

8. The apparatus of claim 7, wherein each transducer subhousing includes a finger for supporting each transducer subhousing rider, the finger being movable to disengage the rider from the transducer support housing rail to permit the lateral adjustment.

9. The apparatus of claim 1, wherein the at least one transducer transmits ultrasound energy.

10. The apparatus of claim 9, wherein the at least one transducer is constructed to apply continuous wave ultrasound energy.

11. The apparatus of claim 1, wherein the fixing device includes a spring-loaded adjustment mechanism for pressing the apparatus against the penis and holding the transducer housing in place.

12. The apparatus of claim 1, wherein the at least one transducer is constructed to transmit/receive energy continuously over an extended period of time to continuously measure penile blood velocity.

13. The apparatus of claim 1, further including an acoustically conductive film and/or gel disposed to improve acoustic conduction between the at least one transducer and the penis.

14. The apparatus of claim 1, wherein the at least one transducer comprises at least two transducers positioned over respective cavernosal arteries in the penis to measure blood flow on both sides of the penis.

15. The apparatus of claim 1, in combination with a male impotence diagnostic system including at least one display device for display of graphical representations indicative of blood velocity in the cavernosal artery.

16. The apparatus of claim 1, wherein the at least one transducer comprises a single transmit/receive transducer.

17. A method of diagnosing male impotence, comprising:
   placing at least one transducer into contact with the penis, the at least one transducer being supported by a transducer housing;
   fixing the transducer housing and the at least one transducer in place on the penis with a fixing device, such that the angular orientation of the at least one transducer with respect to the penis is maintained substantially fixed;
   holding the penis substantially in place with a pressure balloon mechanism; and
   measuring blood flow velocity in the penis using the energy transmitted and received by the at least one transducer.

18. The method of claim 17, further comprising the steps of introducing a vasodilating agent to the penis and subsequently measuring blood flow velocity continuously over an extended period of time.

19. The method of claim 17, further comprising the step of displaying a graphical representation indicative of blood flow velocity on a display device.

20. The method of claim 19, further comprising the step of displaying an electrocardiogram or pulse oximetry output in correlation with the graphical representation of blood flow velocity.

21. A method of diagnosing male impotence, comprising:
   (a) measuring blood flow velocity in at least one cavernosal artery in the penis;
   (b) subsequently introducing a vasodilating agent to the penis to induce an erectile response;
   (c) continuously measuring blood flow velocity in the at least one cavernosal artery over a time period after introduction of the vasodilating agent; and
   (d) continuously measuring the diameter of the penis over the time period of step (c); and
   (e) simultaneously displaying graphical representations of blood flow velocity data and penis diameter data over the time period of step (c).

22. An apparatus for measuring blood velocity in at least one blood vessel of a patient, the blood vessel being contained within a surrounding anatomical structure; the apparatus comprising:
   at least one transducer for transmitting/receiving energy and reading corresponding Doppler effect to detect blood velocity in the at least one blood vessel;
   a transducer housing for supporting the at least one transducer in a substantially fixed orientation with respect to the anatomical structure as the at least one transducer detects blood velocity the transducer housing defining two distal legs and a bend circumferentially therebetween to substantially conform to the outer circumference of the anatomical structure, the transducer housing being out of physical contact with the at least one blood vessel; and
   a fixing device, mechanically coupled to the transducer housing, to substantially mechanically fix the transducer housing in place on the anatomical structure and hold the at least one transducer in a substantially constant angular orientation with respect to the at least one blood vessel.

23. The apparatus of claim 22, wherein the at least one transducer comprises two independently operable transducers.

24. The apparatus of claim 23, wherein one of the transducers is positioned on one of the legs on one side of the bend of the transducer housing to detect blood velocity in a blood vessel within the anatomical structure; further wherein another one of the transducers is positioned on the other of the legs on the other side of the bend of the transducer housing to detect blood velocity in another blood vessel within the anatomical structure.

25. The apparatus of claim 23, wherein the transducer housing is constructed to substantially straddle the anatomical structure; further wherein the transducer housing is constructed to position one of the transducers at substantially a 10 o'clock position about the anatomical structure and another one of the transducers at substantially a 2 o'clock position about the anatomical structure.

26. The apparatus of claim 23, wherein the transducers are independently movable along the legs of the transducer housing.

27. The apparatus of claim 22, wherein the apparatus is constructed to conform to the shape of a male penis; further wherein the transducer housing is constructed to position the at least one transducer to detect blood velocity in a cavernosal artery of the penis without interference from a dorsal blood vessel of the penis.

28. The apparatus of claim 27, wherein the fixing device is constructed to accommodate the changing diameter of the penis between erect and flaccid states thereof.

29. An apparatus for diagnosing male impotence by measuring blood velocity in a cavernosal artery of a male penis, the apparatus comprising:
   at least one transducer for transmitting/receiving energy and reading corresponding Doppler effect to detect blood velocity in the cavernosal artery, the at least one transducer also being constructed to transmit/receive energy to detect a diameter value related to the penis;

a transducer housing for supporting the at least one transducer in a substantially fixed orientation with respect to the penis as the at least one transducer measures blood velocity in the cavernosal artery;

a fixing device, mechanically coupled to the transducer housing, to substantially mechanically fix the transducer housing in place with respect to the penis and hold the at least one transducer in a substantially constant angular orientation with respect to the cavernosal artery during an impotence diagnostic procedure; and a display, operably coupled with the at least one transducer, for displaying the diameter value and the blood velocity.

30. The apparatus of claim 29, wherein the diameter value is selected from the group consisting of penis diameter and cavernosal artery diameter.

31. An apparatus for measuring blood velocity in a cavernosal artery of a male penis, the apparatus comprising:

at least one transducer for transmitting/receiving energy and reading corresponding Doppler effect to detect blood velocity in the cavernosal artery both when the penis is in an erect state and when the penis is in a flaccid state;

a transducer housing for supporting the at least one transducer in a substantially fixed orientation with respect to the penis as the at least one transducer measures blood velocity in the cavernosal artery; and a fixing device, mechanically coupled to the transducer housing, to substantially mechanically fix the transducer housing in place with respect to the penis and hold the at least one transducer in a substantially constant angular orientation with respect to the cavernosal artery during a measurement procedure, the fixing device being constructed to accommodate the changing size of the penis between the erect and flaccid states such that the at least one transducer remains aligned with the cavernosal artery as the size of the penis changes;

wherein the at least one transducer comprises at least two transducers, further wherein the at least two transducers are shiftable relative to each other to aim the transmitted/received energy to a desired location;

further wherein each transducer is supported by a subhousing, each subhousing being slideably supported by the transducer housing, each transducer and respective transducer subhousing being shiftable relative to the transducer housing to aim the transmitted/received energy to a desired location.

32. An apparatus for measuring blood velocity in a cavernosal artery of a male penis, the apparatus comprising:

at least one transducer for transmitting/receiving energy and reading corresponding Doppler effect to detect blood velocity in the cavernosal artery both when the penis is in an erect state and when the penis is in a flaccid state;

a transducer housing for supporting the at least one transducer in a substantially fixed orientation with respect to the penis as the at least one transducer means measures blood velocity in the cavernosal artery, the at least one transducer being shiftable along the transducer housing to aim the transmitted/received energy to a desired location; and a fixing device, mechanically coupled to the transducer housing, to substantially mechanically fix the transducer housing in place with respect to the penis and hold the at least one transducer in a substantially constant angular orientation with respect to the cavernosal artery during a measurement procedure, the fixing device being constructed to accommodate the changing size of the penis between the erect and flaccid states such that the at least one transducer remains aligned with the cavernosal artery as the size of the penis changes.

33. The apparatus of claim 1, wherein the at least one transducer is moveable along the transducer support housing.

34. The apparatus of claim 1, wherein the at least one transducer consists of multiple transducers, the multiple transducers being supported on the transducer support housing such that the multiple transducers are all disposed at a top portion of the penis.

35. The apparatus of claim 1, wherein the fixing device tightens the transducer support housing with respect to the penis.

36. The apparatus of claim 35, wherein the fixing device is flexible.

37. The apparatus of claim 1, wherein the transducer support housing is constructed to support the at least one transducer only on one side of the penis.

* * * * *